US012569305B2

(12) United States Patent  
Ramos

(10) Patent No.: US 12,569,305 B2  
(45) Date of Patent: Mar. 10, 2026

(54) SURGICAL GUIDE SYSTEM FOR ASSISTING A USER CONTROLLING A SURGICAL TOOL

(71) Applicant: Drill Surgeries Ltd, Liverpool (GB)

(72) Inventor: Moises Barbera Ramos, Liverpool (GB)

(73) Assignee: Drill Surgeries Ltd, Liverpool (GB)

( * ) Notice: Subject to any disclaimer, the term of this patent is extended or adjusted under 35 U.S.C. 154(b) by 0 days.

(21) Appl. No.: 18/866,678

(22) PCT Filed: May 19, 2023

(86) PCT No.: PCT/GB2023/051328  
§ 371 (c)(1),  
(2) Date: Nov. 18, 2024

(87) PCT Pub. No.: WO2023/223052  
PCT Pub. Date: Nov. 23, 2023

(65) Prior Publication Data  
US 2025/0160963 A1    May 22, 2025

(30) Foreign Application Priority Data

May 20, 2022    (GB) ..................................... 2207443

(51) Int. Cl.  
*A61B 34/20* (2016.01)  
*A61B 34/10* (2016.01)  
(Continued)

(52) U.S. Cl.  
CPC ............ *A61B 34/20* (2016.02); *A61B 90/361* (2016.02); *A61B 90/96* (2016.02);  
(Continued)

(58) Field of Classification Search  
CPC ........ A61B 34/20; A61B 90/96; G16H 10/00; G16H 20/17; G16H 30/00; G16H 40/60; G16H 70/00; G06F 16/9554  
(Continued)

(56) References Cited

U.S. PATENT DOCUMENTS

| 10,390,891 B2 | 8/2019 | Govari et al. |
| 2015/0164606 A1 | 6/2015 | Jacobs |

(Continued)

FOREIGN PATENT DOCUMENTS

| DE | 102010041914 | 4/2012 |

*Primary Examiner* — Edwyn Labaze  
(74) *Attorney, Agent, or Firm* — Workman Nydegger

(57)    ABSTRACT

A surgical guide system for assisting a user controlling a surgical tool, comprising: a first reference guide member, operably coupleable to a fixed object having at least one predetermined feature, configured to define a first reference frame within a three-dimensional space; a control unit, adapted to capture an image of at least said fixed object and identify, from a predetermined list comprising a plurality of fixed objects, said fixed object, and provide a first input signal indicative of said identified fixed object, further adapted to determine the position and orientation of said at least one predetermined feature relative to said first reference frame based on said first input signal, and provide a first output signal on a visual output device adapted to guide the user moving, positioning and orientating the surgical tool towards and into engagement with said predetermined feature.

20 Claims, 7 Drawing Sheets

(51) Int. Cl.

| | |
|---|---|
| *A61B 90/00* | (2016.01) |
| *A61B 90/50* | (2016.01) |
| *A61B 90/96* | (2016.01) |

(52) U.S. Cl.

CPC . *A61B 2034/107* (2016.02); *A61B 2034/2055* (2016.02); *A61B 2090/0805* (2016.02); *A61B 2090/0806* (2016.02); *A61B 2090/373* (2016.02); *A61B 2090/502* (2016.02)

(58) Field of Classification Search

USPC ...................... 235/375, 487, 462.01, 462.09

See application file for complete search history.

(56) References Cited

U.S. PATENT DOCUMENTS

| | | | |
|---|---|---|---|
| 2017/0323481 A1* | 11/2017 | Tran ..................... | H04N 23/611 |
| 2021/0228220 A1 | 7/2021 | Bettenga | |
| 2021/0322148 A1* | 10/2021 | Mitra .................... | G16H 50/20 |
| 2022/0015835 A1 | 1/2022 | Behera | |
| 2022/0051483 A1* | 2/2022 | Nevins ................. | G06T 19/006 |
| 2022/0096197 A1* | 3/2022 | Song ..................... | A61B 90/36 |
| 2022/0287676 A1* | 9/2022 | Steines ................. | A61B 90/37 |

* cited by examiner (a)

(b)

103

129

111

115

113*

SURGICAL GUIDE SYSTEM FOR ASSISTING A USER CONTROLLING A SURGICAL TOOL

CROSS-REFERENCE TO RELATED APPLICATIONS

The present application is a 35 U.S.C. § 371 U.S. National Stage of International Application No. PCT/GB2023/051328, filed on May 19, 2023, which claims priority to Great Britain Patent Application No. 2207443.9, filed May 20, 2022, the entire content of each of which is incorporated herein by this reference.

The invention relates generally to a surgical guide system. In particular, the invention relates to a surgical guide system for assisting a user controlling a surgical tool, for example to assist the welding of fractured bones during intramedullary nailing surgeries on the femur, tibia and humerus, as well as, femoral-, tibial- and humeral plates; foot hinge nail surgeries and the like.

BACKGROUND

During surgery, a user controls a surgical tool to operate on a patient. One example form of surgery is for the treatment of bone fractures for the femur, tibia and humerus, which aim to weld and stabilise the fractured bone. These surgeries typically involve reaming a segment from a fractured bone to facilitate the passage of an intramedullary nail from one side to the other along the longitudinal axis of the bone. In order to secure the nail within the bone, openings are drilled through the bone, and screws are used to secure the intramedullary nail in place.

Surgical procedures require careful and accurate manipulation of surgical tools in three-dimensional space. This is especially the case in intramedullary nailing surgeries, where it is particularly challenging to locate screw holes and screws required to fixate the intramedullary nail in place. This is exacerbated by the fact that different patients have different bone sizes and structures, which result in fluctuations between screw locations when the intramedullary nail is implanted. Furthermore, depending on the type of intramedullary nail required (i.e. which bone a nail is to be fixed to), different sizes, shapes and configurations of nails are required. These factors affect not only the size and shape of screws required to affix intramedullary nails in place, but also the position and orientation of screws. If screws are not properly aligned with apertures of the intramedullary nail, then a fractured bone cannot be properly stabilised, resulting in complications such as a weakened fractured bone, or the need for redrilling or additional surgeries.

Conventional systems aim to guide the stabilisation process of intramedullary nailing by using X-ray imaging techniques to repeatedly scan the surgical region in order to locate the apertures for affixing screws. However, such systems and techniques require the surgeon to continuously look away from the patient, towards display screens to ensure alignment before drilling which reduces the accuracy of drilling. Known techniques are rigorous for the surgeon, and removes their focus away from the surgical procedure. In addition, these techniques expose the patient to X-ray radiation, which can increase health risks of not only the patient, but those in the operation theatre. Furthermore, conventional guidance systems come with relatively high manufacturing and/or maintenance costs, causing many procedures (e.g. around osteosynthesis) to be conducted without such guidance system, despite the fact, that the use of a guidance system is likely to be beneficial to the outcome of the surgery.

It would be desirable to provide a surgical guide system for assisting a user controlling a surgical tool. Particularly, it is an object of the invention to provide a surgical guide system that improves the accuracy and consistency of surgical procedures. It is another object of the invention to provide a surgical guide system that improves the alignment of surgical tools, and components to be inserted into a patient during surgery. It is a further object of the present invention to provide a surgical guide system with an improved versatility, that can provide user assistance in a number of different surgeries.

The present invention provides at least an alternative to surgical guide systems of the prior art.

SUMMARY OF THE INVENTION

In accordance with the present invention there is provided a surgical guide system according to the appended claims.

According to an aspect of the present invention, there is provided a surgical guide system for assisting a user controlling a surgical tool. The surgical guide system comprises a first reference guide member, operably coupleable to a fixed object having at least one predetermined feature, configured to define a first reference frame within a three-dimensional space; and a control unit, adapted to capture an image of at least the fixed object and identify, from a predetermined list comprising a plurality of fixed objects, the fixed object, and provide a first input signal indicative of the identified fixed object, further adapted to determine the position and orientation of the at least one predetermined feature relative to the first reference frame based on the first input signal, and provide a first output signal on a visual output device, adapted to guide the user moving, positioning and orientating the surgical tool towards and into engagement with the predetermined feature.

Thus, the surgical guide system uses a reference guide operably couplable to a fixed object, along with an identification signal of the fixed object, to determine a position and orientation of a predetermined feature. By determining the position and orientation of that feature in this way, the surgical guide system provides a signal on a visual output device to guide the user to manoeuvre a surgical tool to engage with the feature. This arrangement is particularly beneficial because this provides a more accurate and consistent guide for the surgical tool to be moved towards and to engage with the feature, for a number of different fixed objects (e.g. intramedullary nails). Guidance is therefore provided without the need for X-ray imaging techniques, and without compromising the dexterity of the user during surgical operations.

In some embodiments, the control unit is adapted to capture an image of at least the fixed object and the surgical tool, and identify, from a predetermined list comprising a plurality of fixed objects and surgical tools, the fixed object and the surgical tool.

Advantageously, in some specific embodiments, the first input signal is indicative of the identified fixed object, as well as, the surgical tool. Since the position and orientation is determined based on such a first input signal (i.e. identification of the fixed object and the identification of the surgical tool), the surgical guide system is versatile in the sense that it can provide guidance for moving and orientating the surgical tool into a number of predetermined features, and for a number of different components.

Advantageously, in some embodiments, the surgical guide system further comprises a second reference guide member, operably coupleable to the surgical tool, so as to define a position, orientation and motion of the surgical tool relative to the first reference frame. This is particularly beneficial because uses separate references guides operably coupled to a fixed object and a surgical tool, to determine a position, orientation and motion of the surgical tool relative to the fixed object in three-dimensional space.

Advantageously, in some specific embodiments, the control unit is further adapted to determine the position, orientation and motion of the second reference guide member relative to the first reference guide member, and provide a second output signal on the visual output device, further adapted to guide the user moving, positioning and orientating the surgical tool towards and into engagement with the predetermined feature. Using a reference guide which is operably coupled to the fixed object, in addition to another reference guide operably coupled to the surgical tool, is particularly beneficial because this allows a more accurate relative position, orientation and movement of the surgical tool to be determined relative to the at least one predetermined feature of the fixed object. This allows a signal to be provided to that assists the user to guide the tool surgical relative to and, therefore, towards and into engagement with the predetermined feature.

In some embodiments, the first reference guide member is operably coupleable to a handle member, the handle member removably coupleable to the fixed object. By having a first reference guide member that comprises a handle member removably coupleable to the fixed object, the handle member can be removed from the fixed object when required, and recoupled to the fixed object when required. For example, the handle member can be removed to provide an alternative reference frame within three-dimensional space.

In specific embodiments, the fixed object comprises a surgical device.

In some specific embodiments, the surgical device comprises an intramedullary rod.

In some embodiments, the at least one predetermined feature comprises a mounting hole on an exterior surface of the fixed object.

Advantageously, in some specific embodiments, the visual output device comprises a mixed reality headset. This is particularly beneficial because the headset can be worn directly by the user, which allows the user to continually look towards the fixed object and/or the predetermined feature, without needing to turn or look away. In alternative embodiments, the signal output device comprises a monitor.

In some embodiments, the visual output signal comprises any one of an augmented-reality (AR) and Mixed Reality (XR) visual marker superimposing any one of the at least one predetermined feature.

Advantageously, in some embodiments, the AR and XR visual marker comprises a projection of the at least one predetermined feature onto the fixed object.

In some specific embodiments, the AR and XR visual marker further comprises an extrapolation of the at least one predetermined feature onto an exterior surface within the first reference frame. By providing an extrapolation of the at least one predetermined feature in this way, this provides further guidance of the orientation and projected path of the surgical tool.

In some embodiments, the control unit is operably coupled to any one or a combination of the first reference guide member and the second reference guide member via any one or any combination of a shielded wired connection and a wireless data connection. In some specific embodiments, the wireless data connection is via a light fidelity (Li-Fi) connection. The control unit may be operably coupled to any one or a combination of the first reference guide member and the second reference guide member via a shielded wired connection, which reduces interference with other apparatuses. Alternatively, the control unit may be operably coupled to any one or a combination of the first reference guide member and the second reference guide member via a wireless data connection, which improves the manoeuvrability of the surgical tool in three-dimensional space. Using a light fidelity connection is particular beneficial because this utilises visible light, so does not interfere with radio waves, while improving the manoeuvrability of the surgical tool in three-dimensional space.

Advantageously, in some embodiments, the control unit is adapted to determine the position, orientation and motion of the surgical tool relative to the first reference frame in real time. In this way, the accuracy of positioning, orientating and moving the surgical tool is improved.

Advantageously, in some embodiments, the control unit is adapted to provide an optimised trajectory from the first reference guide member to the second reference guide member and track deviation of the reference guide member from the optimised trajectory.

Advantageously, in some specific embodiments, the control unit is adapted to provide a signal adapted to convey a degree of the deviation from the optimised trajectory.

BRIEF DESCRIPTION OF THE DRAWINGS

Embodiments of the invention are now described, by way of example only, hereinafter with reference to the accompanying drawings, in which.

DETAILED DESCRIPTION

Figure 1:
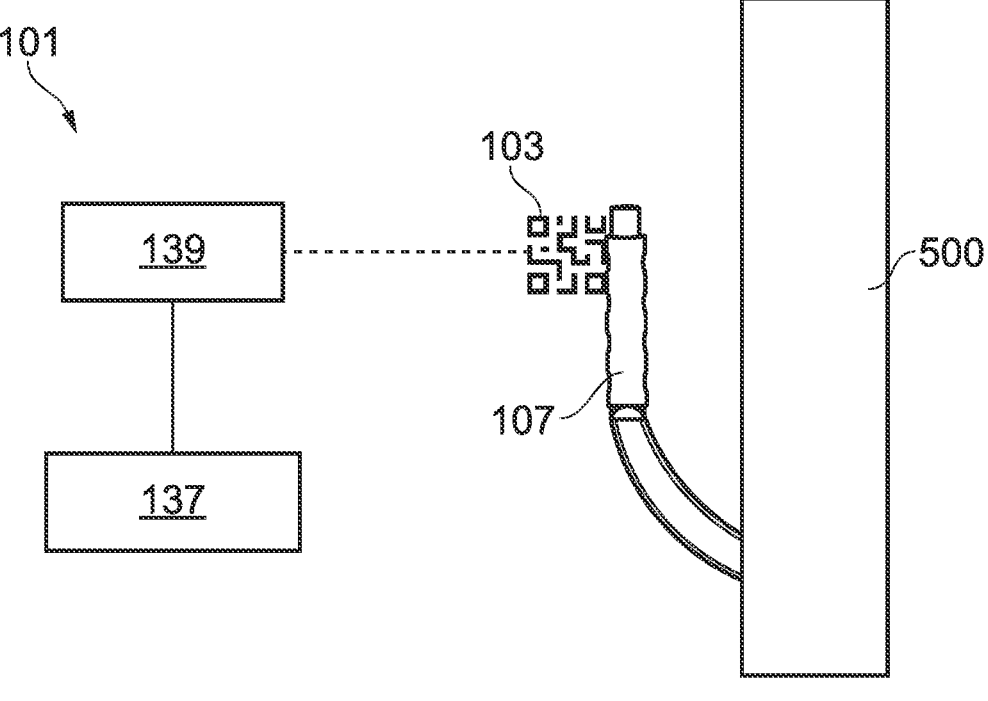
FIG. 1 illustrates a schematic diagram of a surgical guide system including a fixed object.

Certain terminology is used in the following description for convenience only and is not limiting. The words 'right', 'left', 'lower', 'upper', 'front', 'rear', 'upward', 'down' and 'downward' designate directions in the drawings to which reference is made and are with respect to the described component when assembled and mounted. The words 'inner', 'inwardly' and 'outer', 'outwardly' refer to directions toward and away from, respectively, a designated centreline or a geometric centre of an element being described (e.g. central axis), the particular meaning being readily apparent from the context of the description.

Further, as used herein, the terms 'connected', 'attached', 'coupled', 'mounted' are intended to include direct connections between two members without any other members interposed therebetween, as well as, indirect connections between members in which one or more other members are interposed therebetween. The terminology includes the words specifically mentioned above, derivatives thereof, and words of similar import.

Further, unless otherwise specified, the use of ordinal adjectives, such as, "first", "second", "third" etc. merely indicate that different instances of like objects are being referred to and are not intended to imply that the objects so described must be in a given sequence, either temporally, spatially, in ranking or in any other manner.

Like reference numerals are used to depict like features throughout.

Referring now to FIG. 1, there is shown a surgical guide system 101. The system 101 has a reference guide member 103 that is coupled to a fixed object or surgical device 107. The surgical device 107 is a fixed object in the sense that part of the surgical device 107 is implanted into the patient body, for example, into the femur or tibia of a leg 500, thus, the surgical device 107 is fixed relative to the patient. The reference guide member 103 is further used to define a reference frame (131, see FIG. 4a) within a three-dimensional (3D) space (i.e. it defines a 3D coordinate system for the surgical device 107 fixed within the patient).

Figure 2:
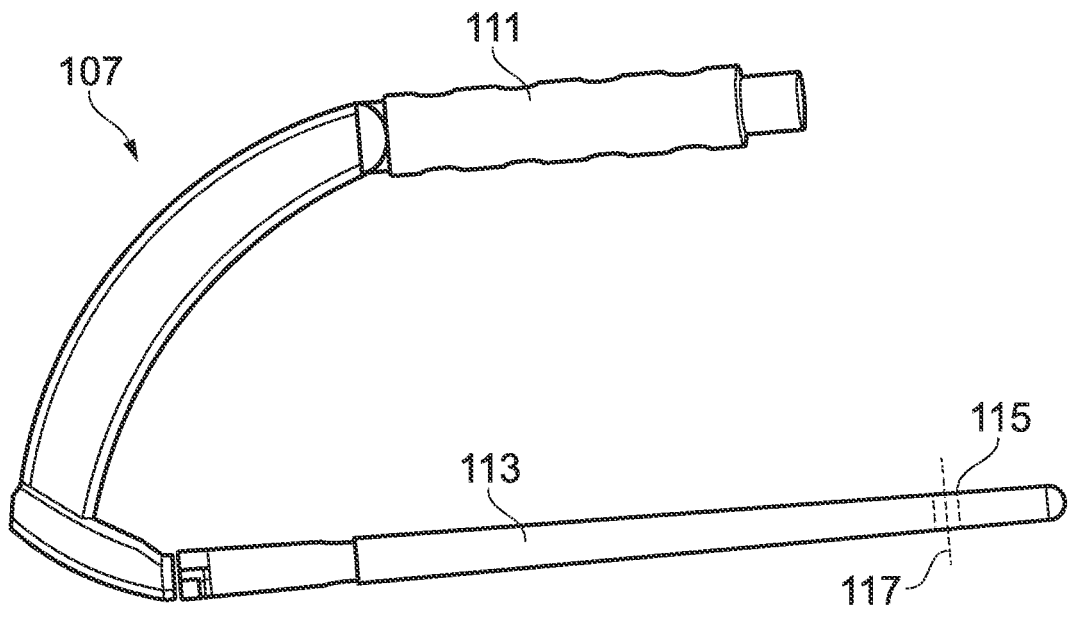
FIG. 2 illustrates a perspective view of fixed object and respective handle, wherein the fixed object is an intermedullary nail having a screw mount.

FIG. 2 shows an example of the surgical device 107, isolated from the patient so as to show more detail. The surgical device 107 illustrated is provided in the form of a hook shape. On one end, there is provided a handle 111, onto which the reference guide member 103 is coupled. On the other end, there is provided an intramedullary nail 113, which is insertable into the patient body (e.g. patient leg 500). The intramedullary nail 113 has a mounting hole 115 on an exterior surface extending from one side to the other. The mounting hole 115 defines a central axis 117. The intramedullary nail 113 and the handle 111 are detachable from and re-attachable to one another. It is understood by the person skilled in the art that any other surgical device 107 (e.g. surgical plates) may be used within the scope of this invention. Also, the handle portion 111 may be provided in any suitable form and attached to the surgical device 107 via any suitable coupling.

The surgical guide system 101 is provided with a control unit 139 (e.g. including controller, sensor, processor) which is connected to and/or has access to a database 137 (wired or wireless connection). The database 137 includes a predetermined list of fixed objects 107. In this example embodiment, the database 137 includes a predetermined list of a plurality of surgical devices, including different types of intramedullary nails for different bones, such as, but not limited to the humerus, femur and tibia. Thus, the different surgical devices in the list have different shapes, sizes and configurations. Alternatively or additionally, the database may include any other type of surgical device, such as, for example, nails or guide surgical plates for the tibia, humerus and femur, or any other part of the human or animal body.

In use, the control unit 139 identifies the fixed object 107 (inserted into the bone) either by visual recognition or from the reference guide member 103 (QR code) to then compare the identified fixed object 107 with the ones provided in the predetermined list of components in database 137. Once the control unit 139 has confirmed the fixed object 107, it provides an input signal indicative of the fixed object 107. The control unit 139 uses the received input signal to determine a position and orientation of at least one predetermined feature (e.g. a mounting hole or thread of the surgical device 107) relative to the reference frame 103. The control unit 139 provides an output signal to a visual output device, in order to guide a user to move, position and orientate the surgical tool 109, 209, 309 towards the predetermined feature (e.g. to place a screw into the fixture on the intermedullary nail 113).

An example of the use of the surgical guide system 101 will now be described with reference in particular to FIGS. 3 to 5.

Figure 3:
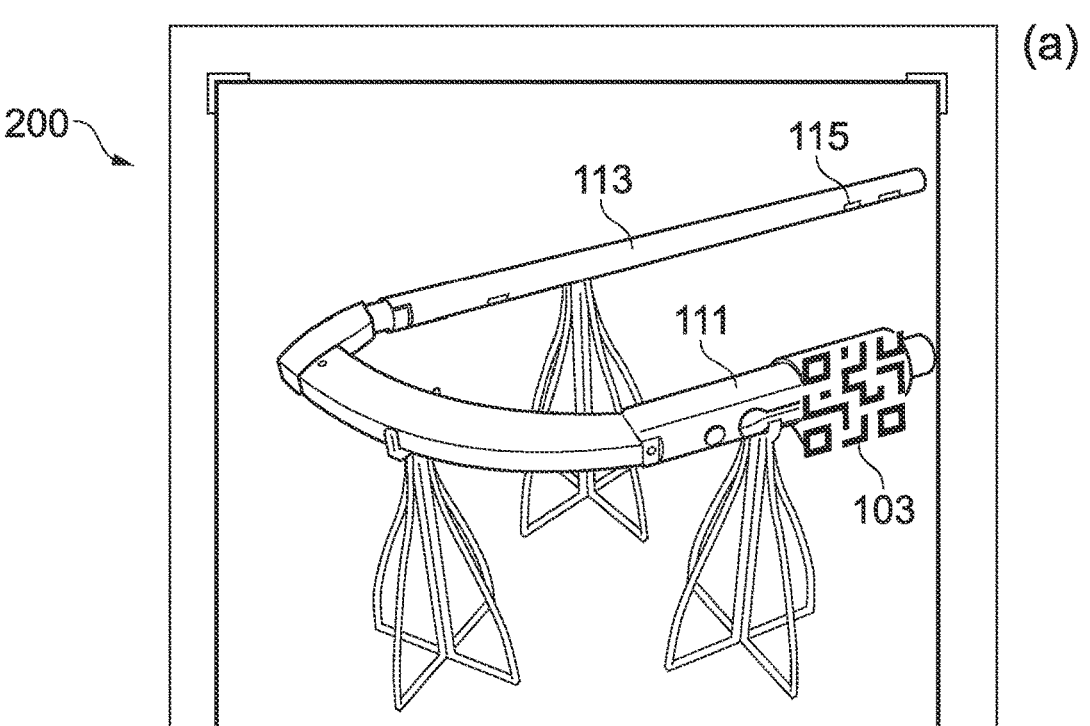
FIG. 3 illustrates an interface showing: (a) a fixed object with first reference guide member; and (b) a close-up view of the first reference guide member.
Figure 3:
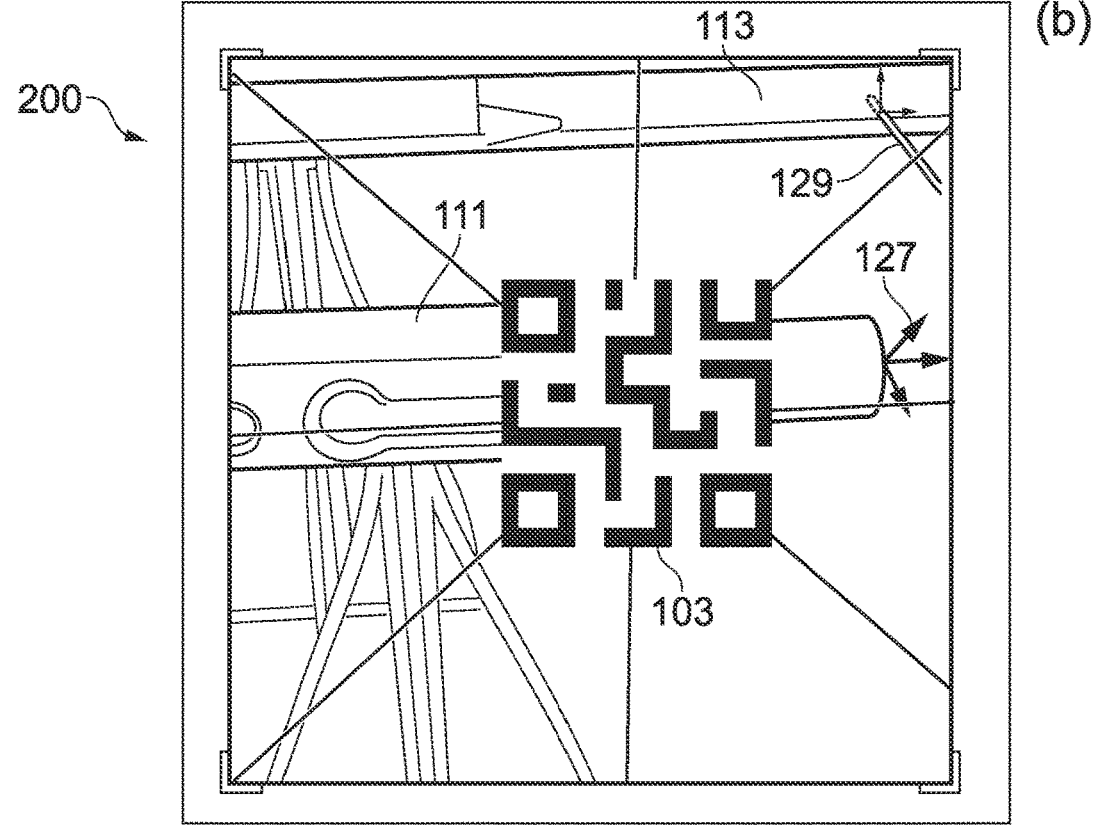
Figure 7:
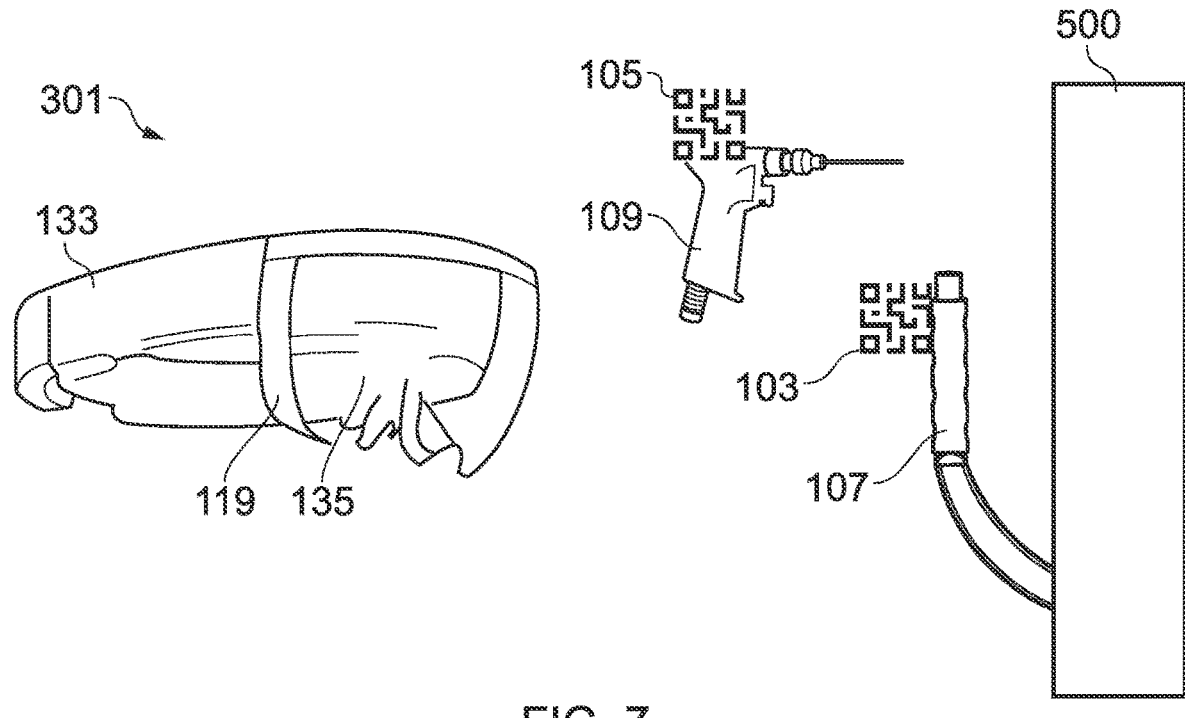
FIG. 7 illustrates a schematic diagram of a surgical guide system including a fixed object and a surgical tool and a visual output device.

As illustrated in FIG. 3, an interface 200 is displayed on a screen of a mixed reality (XR) headset 119 (see FIG. 7, e.g. Microsoft Hololens 2, MagicLeap etc.). These utilise a XR headset 119 to display holograms of the medical equipment and/or implants used and other detailed information to assist the surgeon during the operation in real time. Also, the XR headset 119 may utilises an additional physical QR code or a virtual implementation of Computer Vision algorithms to detect and establish a point of reference in the Operating Room. The operation can be assisted by one single surgeon wearing a single XR Headset 119 or be assisted by a larger number of medical professionals each wearing a respective XR Headsets 119 where all individuals involved can observe the same guidance with the same level of accuracy due to multi-headset interconnectivity which can be done between professionals involved in the same operating room but also with professionals outside the operating room (remote access). This can open an additional level of Surgical Guidance as a result of remote assistance from experts that no longer need to travel to the operating theatre in order to assist a surgeon.

It is understood by the person skilled in the art, that in other embodiments the visual representation of the interface 200 may through any other suitable device, such as, for example, a tablet screen, a smartphone or an external monitor. In this particular example embodiment, the control unit 139 may have access to a camera that is integrated into the XR headset 119 and adapted to capture an image of the fixed reference guide member 103 or any other identifiable feature of the surgical device 107, which is processed to unambiguously identify and find the surgical device 107 within the database 137. In this particular example, the control unit 139 determines the fixed object 107 as an intramedullary nail 113 for the femur. In some example embodiments, the control unit 139 may determine that the handle 111 outside of the patient is attached to an intramedullary nail 113 implanted into the femur, to then recall specific information about the handle 111 and nail 113 assembly from the database 137.

Additionally or instead of the camera integrated into the headset 119, the control unit may have access to an inertial measurement sensor, or to an external handheld camera (e.g. via wireless connection), or the controller 139 may have access to a camera that is integrated into a pair of glasses or goggles.

Figure 4:
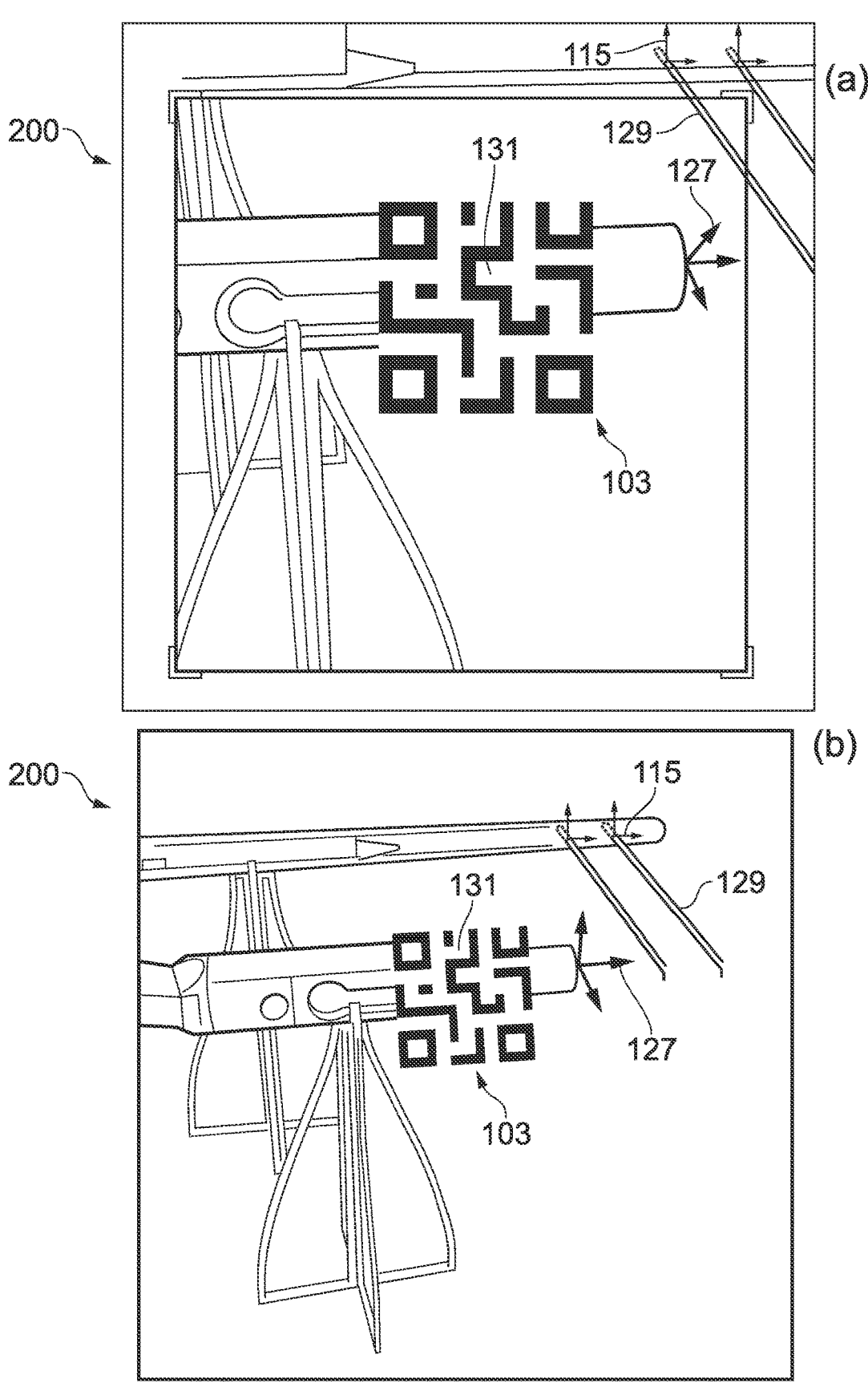
FIG. 4 illustrates an interface showing: (a) a close-up view of the first reference guide with a first reference frame; and (b) a fixed object and an augmented reality visual marker.

Turning to FIG. 4, after the reference guide member 103 is detected, a reference frame 131 is defined within a XYZ coordinate system. The reference frame 131 may or may not be displayed within the headset (or screen) 119. However, the reference frame 131 is used to determine the position and orientation of the predetermined feature (e.g. a mounting hole 115) based on the identification signal provided by the control unit 139. Since the fixed object 107 is determined to be an intramedullary nail 113 for the femur, the predetermined position and orientation of the mounting holes 115 of the intramedullary nail 113 are thus known in relation to the reference frame 131. The position and orientation of the mounting holes 115 relative to the intramedullary nail 113 may, for example, be stored in a library of data (e.g. within the database 137) that includes the positions and orientations of various predetermined features of various components (e.g. the list of surgical devices 107). An augmented reality (AR) or XR visual marker is then projected onto the intramedullary nail 113, so as to intersect with the mounting holes of the nail 113 (location and orientation). As shown, in this particular example embodiment, the AR or XR visual marker includes an extrapolation 129 of the mounting holes 115 along the centre axis of respective mounting holes 115 onto an exterior surface (e.g. of the patient's leg) and within the reference frame 131. The extrapolation 129 of the mounting holes 115 extends beyond the exterior surface of the intramedullary nail 113. It is noted that additional frames of reference may be provided and may additionally be displayed. For example, an intermediate reference frame 127 may also be provided at the tip of the handle 111 as a further reference to determine the position and orientation of the mounting holes 115 relative to the handle portion 111.

Figure 5:
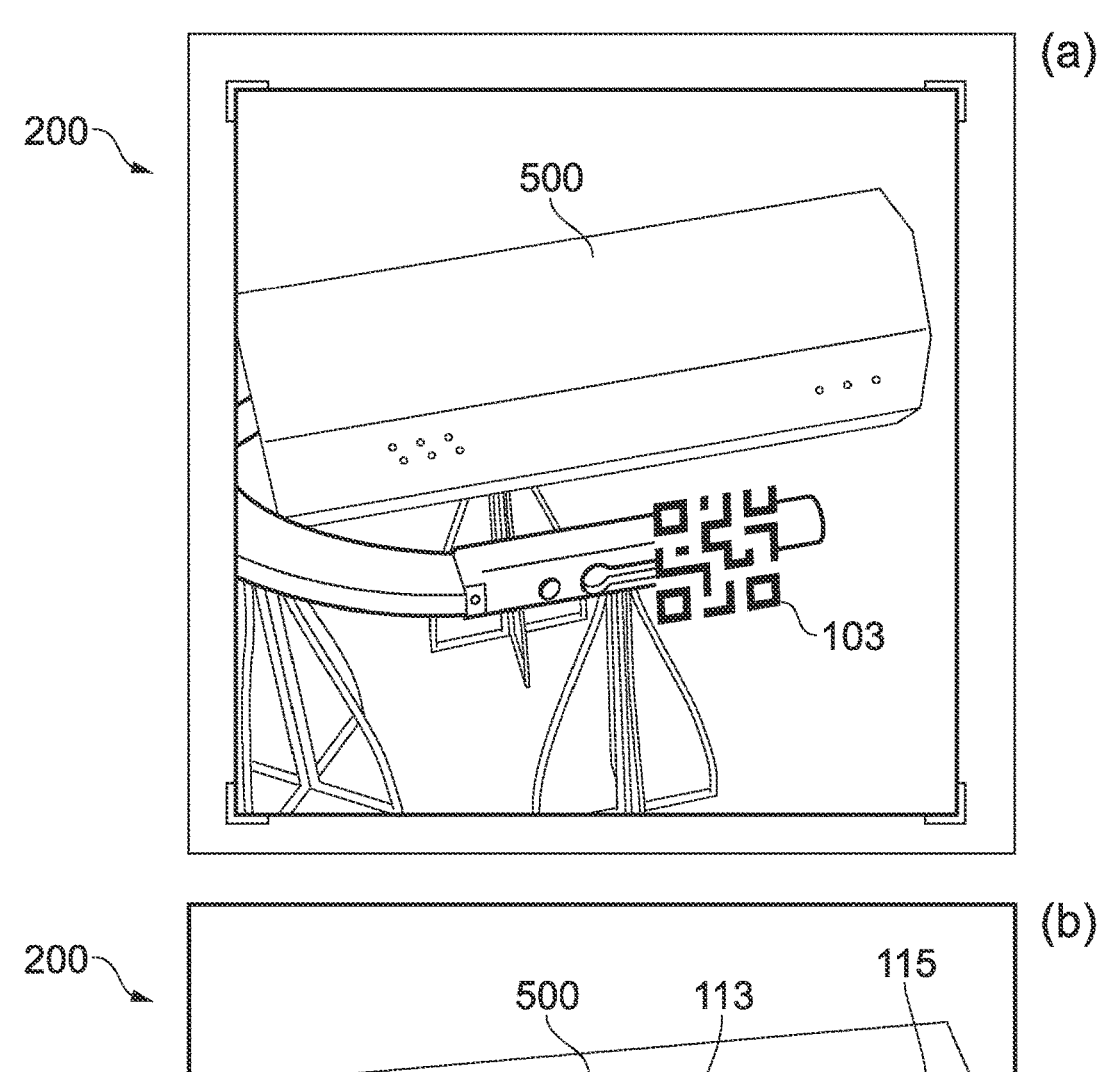
FIG. 5 illustrates an interface showing: (a) a intramedullary nail inside a model patient leg; and (b) a visual output of an intramedullary nail projected onto a model patient leg, and showing an augmented reality visual marker.

FIG. 5 shows an interface 200 displayed on a screen (or with a XR headset 119), where the intramedullary nail 113 is fixed within the leg 500 of a patient. Even though the implanted intramedullary nail 113 is obstructed by the patient's leg 500, the present invention is able to project a visual representation of the intermedullary nail 113 onto the leg surface in line with the actual orientation of the implanted nail 113. In particular, the reference frame 131 is used to determine the position and orientation of the intramedullary nail 113 and the corresponding mounting holes 115, based on the information stored in the database 137. Thus, even if particular features of interest (e.g. mounting holes) are obstructed, an AR or XR visual marker of the obstructed feature can be projected onto the used display (e.g. screen, headset, tablet etc.). Using the reference frame 131 of the reference guide 103, the actual position and orientation of the intramedullary nail 113 within the reference frame 131 is known, and can thus be projected onto the patient leg 500. Additionally, the position and orientation of the mounting holes 115 are projected onto the patient leg 500 by extrapolating the mounting hole 115 (shape, diameter) along the mounting holes 115 central axis.

Figure 6:
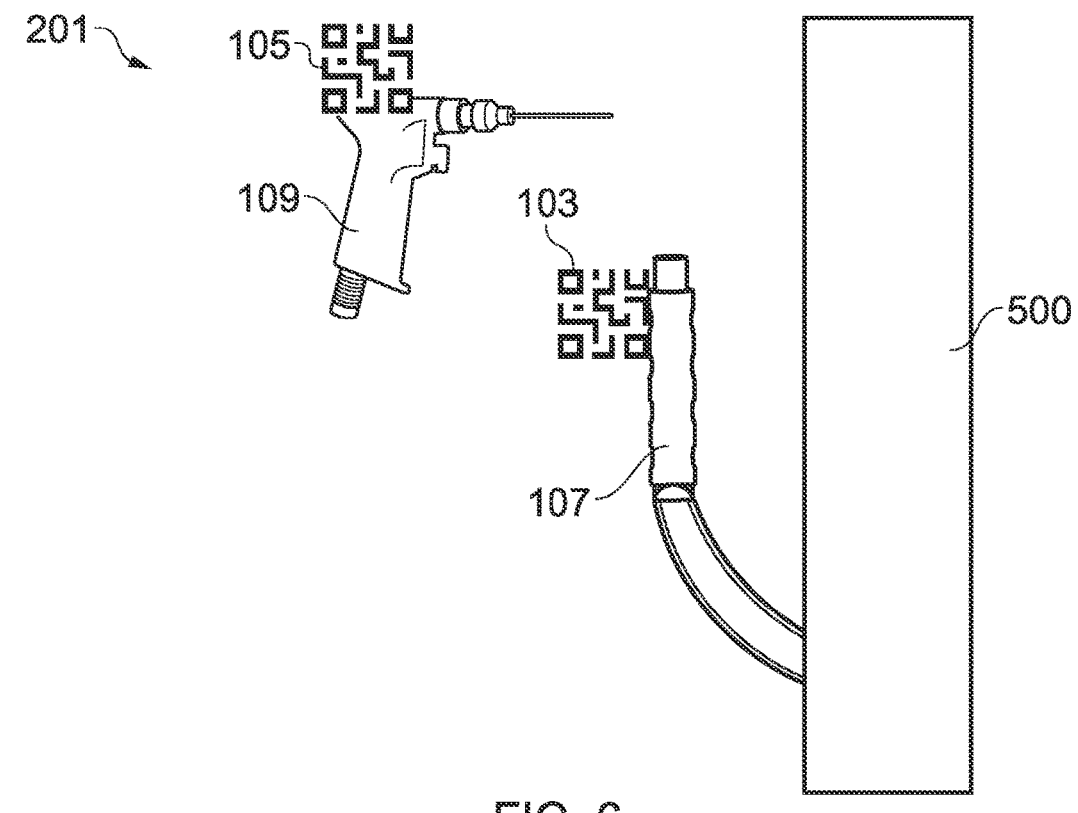
FIG. 6 illustrates a schematic diagram of a surgical guide system including a fixed object and a surgical tool.

FIG. 6 shows another embodiment of the present invention in form of a surgical guide system 201. Here, an additional reference guide member 105 is coupled to a surgical tool 109 (e.g. a drill) so as to define another reference frame (for the tool 109) within a three-dimensional space. For example, the reference frame may be a XYZ coordinate frame. From the reference frame 131 of the fixed reference guide member 103, the tool reference guide member 105 defines the position, orientation and motion of the surgical tool 109 relative to the reference frame. The reference guide members 103, 105 may take the form of an image target (e.g. QR code), whereby the control unit 139 incorporates an image sensor (e.g. camera) so as to determine the position, orientation and motion of the tool reference guide member 105 relative to the fixed reference guide member 103. Since the tool reference guide member 105 is coupled to the surgical tool 109, the position, orientation and motion of the tool 109 is determined relative to the reference frame. This, in turn, provides an output signal to an output device to assist the user in guiding the surgical tool 109 relative to the predetermined features (e.g. mounting holes 115). The output device may be any AR or XR headset or an external monitor (screen, tablet, phone etc.). In this particular example, the control unit 139 is further adapted to provide an optimised trajectory between the fixed reference guide member 103 and the tool reference guide member 105. The control unit 139 may also be adapted to track any deviation from that optimised trajectory, as well as, providing suitable signals (visually in AR or XR, or audibly) to convey the degree of deviation from the optimised trajectory. It is understood by the person skilled in the art, that only one reference guide member is sufficient to provide a reference frame for both, the surgical device 107 and a surgical tool (e.g. drill) moving relative to the surgical device 107, and additional reference guide members (e.g. QR codes) may simply be used to provide information of the tool 109.

FIG. 7 shows yet another example embodiment of the present invention in form of a surgical guide system 301 where the output signal for the tool 109 and surgical device 107 is provided to a mixed reality headset 119. The headset 119 is provided with a headband 133 for attaching on a user's head. The headset 119 is further provided with a display 135 allowing the user to see the real world as well as digital elements overlayed onto the real world objects (AR, XR). The headset 119 is used to receive an output signal to guide the user to manoeuvre the surgical tool 109. Again, FIG. 7 illustrates the surgical tool 109 with a reference guide member 105, though, a single reference guide member on any one of the tool or the surgical device is sufficient.

Figure 8A:
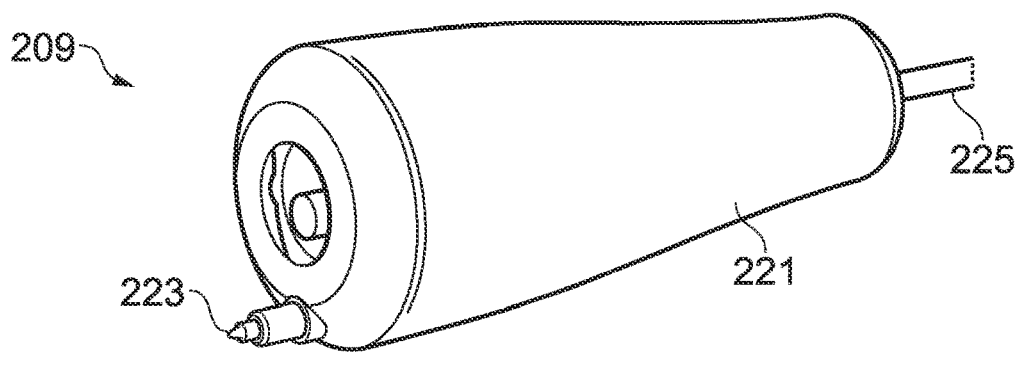
FIG. 8 illustrates a perspective view of a surgical tool having: (a) a marker; and (b) a scalpel.
Figure 8B:
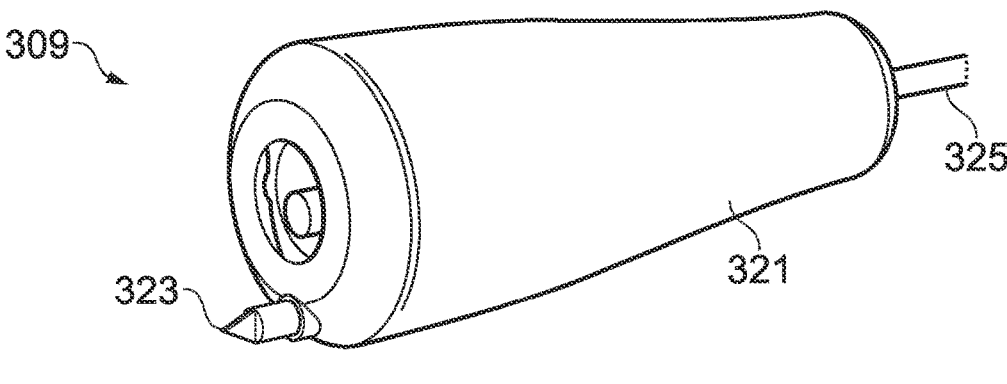
Figure 9:
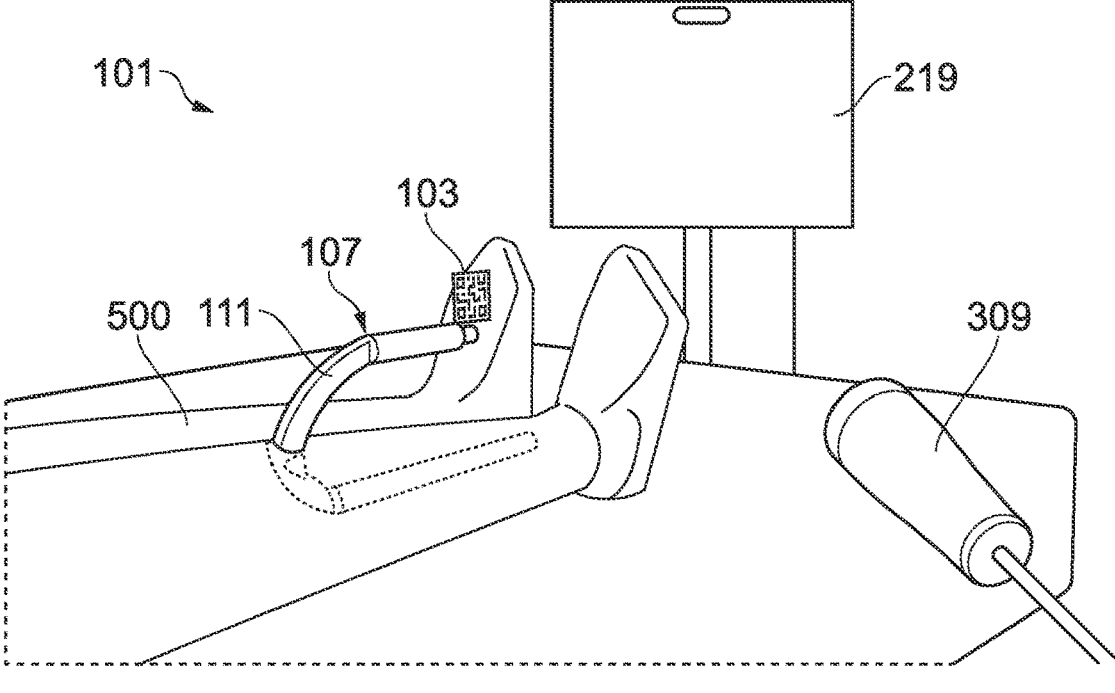
FIG. 9 illustrates a surgical guide system including a display, within an operation theatre environment.

Alternative examples of the surgical tool 109 shown in FIGS. 6 and 7 (e.g. drill) are shown in FIGS. 8 and 9. One example surgical tool 209 includes a tool housing 221 coupled with a marker 223. A camera is provided within the housing 221, which is connected to a control unit, for example, via a shielded wire connection 225. Another example surgical tool 309 includes all the features of the surgical tool 209, but the marker 223 is replaced by a scalpel 323. A camera is provided within the housing 321 that is connected to a control unit, for example, via a shielded wire connection 325. Alternative ways of connecting the camera to the control unit are envisaged, such as, for example, a wireless connection (e.g. a light fidelity (Li-Fi) connection).

A typical setup of an operating theatre environment is illustrated in FIG. 9. Here, a fixed object 107 is inserted into a leg 500 of a patient. A handle 111 of the fixed object 107 comprises a fixed reference guide member 103. A surgical tool 309 comprises a camera that is wirelessly connected to the controller 139 in order to access a database 137 including a plurality of different surgical devices. The control unit 139 is adapted to identify the fixed object 107 and retrieves required information from the database 137. After identifying the fixed object 107 as an intramedullary nail for a femur, the control unit 139 uses the information and an established reference frame to determine a position and orientation of respective mounting holes relative to the reference frame (and leg 500). The control unit 139 further provides an output signal onto a visual output device in order to guide a user to move, position and orientate the surgical tool 309 towards the mounting holes. In this particular illustrated example, the visual output device is an external monitor 219 placed in front of the user.

In some example embodiments, the database 137 includes a predetermined list of a plurality of surgical devices and surgical tools. The predetermined list of surgical tools may, for example, include surgical drills, clips, scalpels, markers, and the like. The control unit may identify both the fixed object and the used surgical tool. Using that identification information, the control unit determines a position and orientation of mounting holes relative to the reference frame. The control unit then provides an output signal onto a visual output device to guide a user to move, position, and orientate a surgical tool 309 towards mounting holes. The surgical tool may, for example, be a scalpel (or a marker pen) held by the surgeon to mark a spot of a mounting hole's location onto the skin of a patient.

In summary, the control unit is adapted to capture an image of at least the fixed object. The control unit may additionally capture an image of the surgical tool. The database includes a list of a predetermined plurality of fixed object, and the list may additionally include a predetermined plurality of surgical tools. The control unit provides a first input signal, which may either by indicative of the identified fixed object alone, or may additionally be indicative of the used surgical tool.

Figure 10:
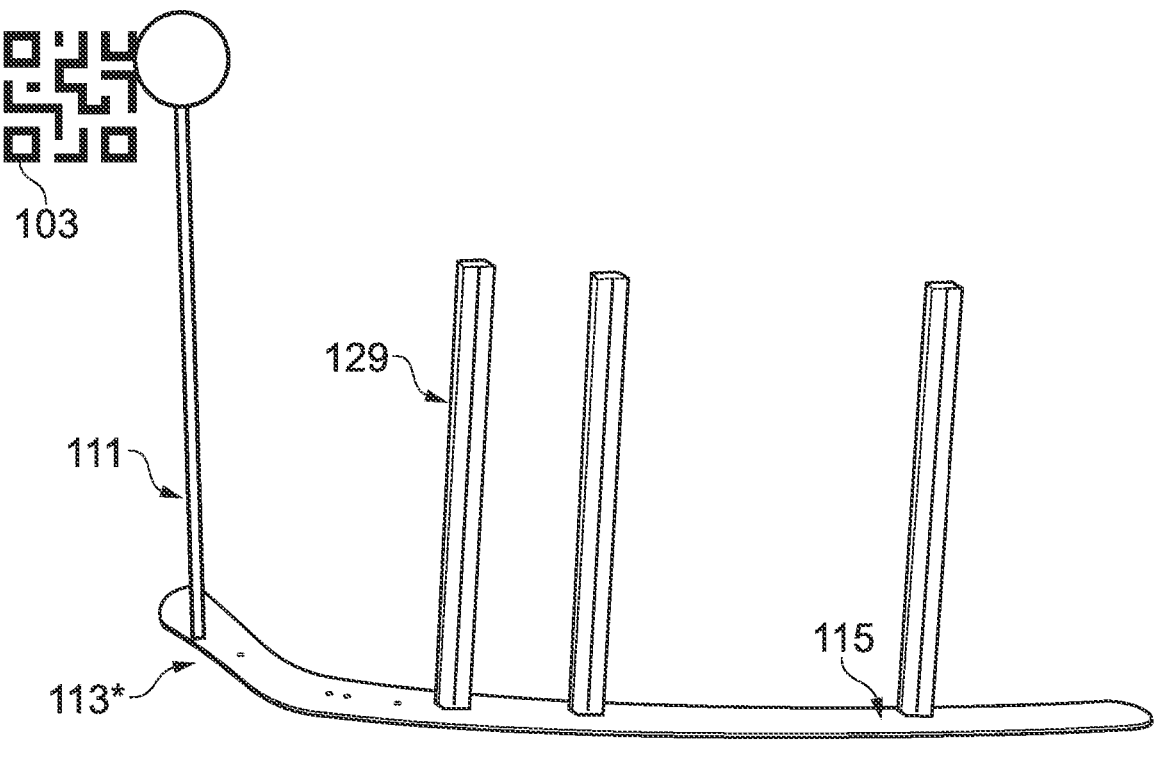
FIG. 10 illustrates a perspective XR view of another fixed object with a reference guide member attached to a handle portion, wherein the fixed object is a plate having a plurality of through holes for fixation and overlayed XR projections of the through holes.

FIG. 10 shows another example of a fixed object 107 in the form of an internal plate 114 (bone plate) in a perspective XR view with a reference guide member 103 attached to a handle portion 111. The bone plate 114 has multiple through holes 115 for fixing the plate 114 to the bone via screws. In this particular XR view, digital image projections and extrapolations 129 are aligned with respective centre axes of the through holes 115.

It will be appreciated by persons skilled in the art that the above detailed examples have been described by way of example only and not in any limitative sense, and that various alterations and modifications are possible without departing from the scope of the invention as defined by the appended claims. Various modifications to the detailed examples described above are possible.

Through the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract or drawings), or to any novel one, or any novel combination, of the steps of any method or process so disclosed.

It will be appreciated by persons skilled in the art that the above embodiment(s) have been described by way of example only and not in any limitative sense, and that various alterations and modifications are possible without departing from the scope of the invention as defined by the appended claims. Various modifications to the detailed designs as described above are possible.

COMPONENT LIST AND REFERENCE NUMERALS

101, 201, 301 Surgical guide system
103 Fixed reference guide member
105 Tool reference guide member
107 Fixed object/surgical device
109, 209, 309 Surgical tool
111 Handle
113 Intramedullary nail
115 Mounting hole
117 Central axis
119 Headset
127 Handle reference frame
129 Extrapolation
131 Fixed reference frame
133 Headband
135 Display
137 Database
139 Control unit
200 Interface
219 Monitor
221, 321 Tool housing
223 Marker
225, 325 Wired connection
323 Scalpel
500 Patient leg

The invention claimed is:

1. A surgical guide system for assisting a user controlling a surgical tool, comprising:

(a) a first reference guide member which includes a QR code and which can be coupled to a selected surgical device for implantation in a patient having at least one mounting hole formed in it, the first reference guide member defining a first reference frame within a three-dimensional space that is fixed relative to the implanted surgical device and thereby defines a reference coordinate system internal to the patient;

(b) a control unit which includes a database containing a library of pre-stored geometric models of surgical devices, each model defining spatial relationships between the location of the marker and predetermined mounting hole geometries of the corresponding surgical devices, (c) a camera which can be accessed by the control unit for capturing an image of the said QR code; and (d) a mixed reality headset;

in which the control unit (i) uses the image of the QR code to identify the selected surgical device from the said plurality of surgical devices, (ii) provides an identification signal indicative of the selected surgical device, (iii) determines, without requiring intraoperative imaging or patient specific reconstruction, the position and orientation of said at least one mounting hole relative to said first reference frame based on the geometric model, and (iv) provides a first output signal to the mixed reality headset which causes a visual marker to be displayed on the headset that projects and extrapolates the central axis of the at least one mounting hole onto an exterior surface of the patient, superimposed on a mixed-reality view of the patient in alignment with the internal mounting hole.

2. A surgical guide system according to claim 1, wherein said first reference guide member is operably coupleable to a handle member, said handle member removably coupleable to said selected surgical device.

3. A surgical guide system according to claim 1, wherein the library of data contains data relating to a plurality of surgical tools and said control unit is further configured to identify a selected surgical tool, from said plurality of surgical tools, and wherein said identification signal is indicative of said identified surgical device and the selected surgical tool.

4. A surgical guide system according to claim 1, further comprising a second reference guide member, operably coupleable to a selected surgical tool, so as to define a position, orientation and motion of the surgical tool within the first reference frame defined by the first reference guide member fixed to the implanted surgical device.

5. A surgical guide system according to claim 4, wherein said control unit is further adapted to determine the position, orientation and motion of said second reference guide member relative to said first reference guide member, and provide a second output signal on said mixed reality headset, further adapted to guide the user moving, positioning and orientating the surgical tool towards and into engagement with said mounting hole.

6. A surgical guide system according to claim 4, wherein said control unit is adapted to provide an optimised trajectory from said first reference guide member to said second reference guide member and track deviation of said reference guide member from said optimised trajectory.

7. A surgical guide system according to claim 6, wherein said control unit is adapted to provide a signal adapted to convey a degree of the deviation from said optimised trajectory.

8. A surgical guidance system comprising:
(a) a plurality of reference guide members, each including a machine-readable marker;
(b) a plurality of surgical devices, each of which is coupleable to one of the reference guide members and has at least one predetermined feature;
(c) a control unit having access to a database containing pre-stored geometric models defining, for each surgical device, spatial relationships between the respective marker and the predetermined features of that device; and
(d) a visual output device configured to display a mixed-reality visualization of at least one of said surgical devices,
wherein the control unit identifies, from the captured markers, at least two of the surgical devices simultaneously, retrieves the corresponding geometric models from the database, and determines spatial relationships among the identified devices within a common reference coordinate system fixed relative to one of the devices.

9. The system of claim 8, wherein the control unit is configured to display, in the mixed-reality visualization, an extrapolated projection of a predetermined feature of a first device in alignment with a predetermined feature of a second device.

10. The system of claim 8, wherein the visual output device comprises a mixed-reality headset that displays holographic markers representing the positions and orientations of the identified surgical devices within the patient.

11. The system of claim 8, wherein the control unit determines the position and orientation of each identified device without using intraoperative imaging or anatomical reconstruction data.

12. The system of claim 8, wherein the database comprises geometric models for multiple implant sizes and configurations, and the control unit selects the model corresponding to the specific implant identified by its marker.

13. The system of claim 8, wherein the control unit computes a trajectory connecting a mounting hole of a first implant and a corresponding opening of a second implant, and provides a visual alignment guide to assist positioning.

14. The system of claim 8, wherein the visual output device simultaneously displays the extrapolated axes of a plurality of mounting holes for multiple implants within a common patient coordinate frame.

15. A surgical guidance system comprising:
(a) a reference guide member coupleable to a surgical device and including a machine-readable marker;
(b) a control unit configured to determine, based on a geometric model stored in a database, the position and orientation of at least one predetermined feature of the surgical device relative to a reference frame defined by the marker; and
(c) a plurality of mixed-reality headsets, each communicatively linked to the control unit,
wherein the control unit transmits synchronized mixed-reality visualizations to the headsets such that multiple users view, in real time, a common projected alignment of the predetermined feature relative to the patient anatomy.

16. The system of claim 15, wherein the control unit updates the visualization in response to movement of the reference guide member, maintaining synchronization among all headsets.

17. The system of claim 15, wherein each mixed-reality headset displays an extrapolated projection of a mounting-hole axis onto the external surface of the patient, visible to all users in the same spatial position.

18. The system of claim 15, wherein one of the mixed-reality headsets is located at a remote site, and the control unit synchronizes the visualization across a communication network to allow remote surgical guidance.

19. The system of claim 15, wherein the control unit provides user-specific overlays to each headset while maintaining a shared spatial reference frame.

20. The system of claim 15, wherein the database includes geometric calibration data used to align the visual projections displayed on different headsets.

* * * * *